United States Patent
Resheski-Wedepohl et al.

(10) Patent No.: US 6,599,521 B1
(45) Date of Patent: Jul. 29, 2003

(54) ABSORBENT ARTICLES FOR THE INHIBITION OF EXOPROTEIN PRODUCTION FROM GRAM POSITIVE BACTERIA

(75) Inventors: Kim L. Resheski-Wedepohl, Reedsville, WI (US); Rae Ellen Syverson, Fond du Lac, WI (US); David C. Potts, Dunwoody, GA (US); Matthew D. Young, N. Augusta, SC (US); Ali Yahiaoui, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/724,190

(22) Filed: Nov. 28, 2000

(51) Int. Cl.⁷ .................................................. A61F 6/06
(52) U.S. Cl. ...................... 424/430; 424/422; 424/443; 424/78.08; 424/402; 424/406
(58) Field of Search ................................ 424/402, 406, 424/422, 431, 443, 430, 78.08; 604/317, 358, 360, 378

(56) References Cited

U.S. PATENT DOCUMENTS

| | | | |
|---|---|---|---|
| 4,405,323 A | 9/1983 | Auerbach | 604/285 |
| 4,413,032 A | 11/1983 | Hartmann et al. | 428/288 |
| 4,413,986 A | 11/1983 | Jacobs | 604/14 |
| 4,424,054 A | 1/1984 | Conn et al. | 604/11 |
| 4,431,427 A | 2/1984 | Lefren et al. | 604/285 |
| 4,585,792 A | 4/1986 | Jacob et al. | 514/474 |
| 4,722,936 A | 2/1988 | Jacob | 514/474 |

(List continued on next page.)

FOREIGN PATENT DOCUMENTS

| | | |
|---|---|---|
| EP | 0 009 977 A1 | 4/1980 |
| EP | 0 053 221 A2 | 6/1982 |
| EP | 0 110 793 B1 | 6/1984 |
| EP | 0 391 741 A2 | 10/1990 |
| EP | 0 395 099 A2 | 10/1990 |
| EP | 0 483 812 B1 | 5/1992 |
| EP | 0 483 835 A1 | 5/1992 |
| EP | 0 683 260 A2 | 11/1995 |
| GB | 1068667 | 5/1967 |
| WO | WO 87/03208 | 6/1987 |
| WO | WO 94/22501 | 10/1994 |
| WO | WO 98/09662 | 3/1998 |
| WO | WO 98/41179 | 9/1998 |
| WO | WO 99/12505 | 3/1999 |
| WO | WO 99/61079 | 12/1999 |

OTHER PUBLICATIONS

Matsumura et al., Surface Activities, Biodegradability and Antimicrobial Properties of n–Alkyl Glucosides, Mannosides and Galactosides, *J. of the Amer. Oil Chem. Soc.*, Dec. 1990, pp. 996–1001, vol. 67, No. 12, The American Oil Chemists' Society.

Bohach et al., Staphylococcal and Streptococcal Pyrogenic Toxins Involved in Toxic Shock Syndrome and Related Illnesses, Microbiology, 1990, 17(4): 251–272.

Projan, et al., Glycerol Monolaurate Inhibits the Production of βLactamase, Toxic Shock Syndrome Toxin–1, and Other Staphylococcal Exoproteins by Interfacing with Signal Transduction, J. Bacteriology Jul., 1994, 176: 4204–4209.

*Primary Examiner*—Thurman K. Page
*Assistant Examiner*—Liliana Di Nola-Baron
(74) *Attorney, Agent, or Firm*—Senniger, Powers, Leavitt & Roedel

(57) ABSTRACT

An absorbent article for inhibiting the production of exoproteins from Gram positive bacteria, such as potentially harmful proteins produced by Staphylococcus species, is described. The absorbent article is particularly useful for inhibiting the production of TSST-1, alpha-toxin and/or enterotoxins A, B and C from *S. aureus* bacterium. An alkyl polyglycoside is incorporated into the absorbent article. For example, alkyl polyglycoside may be coated on the fibers of a liquid-permeable cover of a catamenial tampon.

26 Claims, 2 Drawing Sheets

U.S. PATENT DOCUMENTS

| | | | |
|---|---|---|---|
| 4,722,937 A | 2/1988 | Jacob et al. | 514/474 |
| 4,769,021 A | 9/1988 | Kass | 604/367 |
| 4,952,211 A | 8/1990 | Snider | 604/285 |
| 5,000,749 A | 3/1991 | LeVeen et al. | 604/904 |
| 5,070,889 A | 12/1991 | LeVeen et al. | 128/830 |
| 5,071,648 A | 12/1991 | Rosenblatt | 424/78.06 |
| 5,156,164 A | 10/1992 | LeVeen et al. | 128/832 |
| 5,221,693 A | 6/1993 | Shetty | 514/635 |
| 5,270,032 A | 12/1993 | Pollock et al. | |
| 5,342,331 A | 8/1994 | Silber et al. | 604/330 |
| 5,389,374 A | 2/1995 | Brown-Skrobot | 424/431 |
| 5,476,455 A | 12/1995 | Silber | 604/330 |
| 5,498,252 A | 3/1996 | Silber | 604/330 |
| 5,527,892 A | 6/1996 | Borsotti et al. | 536/18.6 |
| 5,540,979 A | 7/1996 | Yahiaoui et al. | 428/212 |
| 5,547,985 A | 8/1996 | Brown-Skrobot et al. | 514/546 |
| 5,601,814 A | 2/1997 | Barton et al. | 424/85.2 |
| 5,612,045 A | 3/1997 | Syverson | 424/402 |
| 5,618,554 A | 4/1997 | Syverson | 424/431 |
| 5,641,503 A | 6/1997 | Brown-Skrobot | 424/431 |
| 5,679,369 A | 10/1997 | Brown-Skrobot | 424/431 |
| 5,685,872 A | 11/1997 | Syverson | 604/360 |
| 5,705,182 A | 1/1998 | Brown-Skrobot | 424/431 |
| 5,719,113 A * | 2/1998 | Fendler et al. | 510/382 |
| 5,753,252 A | 5/1998 | Brown-Skrobot | 424/431 |
| 5,770,543 A | 6/1998 | Garst et al. | 504/116 |
| 5,814,567 A | 9/1998 | Yahiaoui et al. | 442/118 |
| 5,817,047 A | 10/1998 | Osborn, III et al. | 604/14 |
| 5,932,495 A | 8/1999 | Boney et al. | 442/121 |
| 5,945,175 A | 8/1999 | Yahiaoui et al. | 427/534 |
| 6,017,832 A | 1/2000 | Yahiaoui et al. | 442/118 |
| 6,028,016 A | 2/2000 | Yahiaoui et al. | 442/118 |
| 6,039,716 A | 3/2000 | Jessup et al. | 604/385.1 |
| 6,060,636 A | 5/2000 | Yahiaoui et al. | 604/367 |
| 6,063,335 A | 5/2000 | Pirolo et al. | |
| 6,107,268 A | 8/2000 | Yahiaoui et al. | 510/438 |
| 6,149,934 A | 11/2000 | Krzysik et al. | |
| 6,159,924 A * | 12/2000 | Weller et al. | 510/384 |
| 6,177,367 B1 | 1/2001 | Mathis | |
| 6,231,557 B1 * | 5/2001 | Krautkramer et al. | 604/385.16 |
| 6,296,936 B1 | 10/2001 | Yahiaoui et al. | |
| 6,350,711 B1 | 2/2002 | Potts et al. | |
| 6,410,039 B1 | 6/2002 | Walker | |

\* cited by examiner

ABSORBENT ARTICLES FOR THE INHIBITION OF EXOPROTEIN PRODUCTION FROM GRAM POSITIVE BACTERIA

BACKGROUND

Disposable absorbent devices for the absorption of human exudates are widely used. These disposable absorbent devices typically have a mass of absorbent formed into a desired shape, which is typically dictated by the intended consumer use. In the area of a catamenial tampon, the disposable absorbent article is intended to be inserted in a body cavity for absorption of the body fluids generally discharged during a woman's menstrual period.

There exists in the female body a complex process which maintains the vagina and physiologically related areas in a healthy state. In a female between the age of menarche and menopause, the normal vagina provides an ecosystem for a variety of microorganisms. Bacteria are the predominant type of microorganism present in the vagina; most women harbor about $10^9$ bacteria per gram of vaginal exudate. The bacterial flora of the vagina is comprised of both aerobic and anaerobic bacteria. The more commonly isolated bacteria are Lactobacillus species, corynebacteria, *Gardnerella vaginalis*, Staphylococcus species, Peptococcus species, aerobic and anaerobic Streptococcal species and Bacteroides species. Other microorganisms that have been isolated from the vagina on occasion include yeasts (e.g., *Candida albicans*), protozoas (e.g., *Trichomonas vaginalis*), mycoplasmas (e.g., *Mycoplasma hominis*), chlamydias (e.g., *Chlamydia trachomatis*) and viruses (e.g., *Herpes simplex*). These latter organisms are generally associated with vaginitis or venereal disease, although they may be present in low numbers without causing symptoms.

Physiological, social and idiosyncratic factors affect the quantity and species of bacteria present in the vagina. Physiological factors include age, day of the menstrual cycle and pregnancy. For example, vaginal flora present in the vagina throughout the menstrual cycle can include Lactobacillus species, corynebacterium and mycoplasma. Social and idiosyncratic factors include method of birth control, sexual practices, systemic disease (e.g., diabetes) and medication.

Bacterial proteins and metabolic products produced in the vagina can affect other microorganisms and the human host. For example, the vagina between menstrual periods is mildly acidic having a pH ranging from about 3.8 to about 4.5. This pH range is generally considered the most favorable condition for the maintenance of normal flora. At that pH, the vagina normally harbors the numerous species of microorganisms in a balanced ecology, playing a beneficial role in providing protection and resistance to infection and makes the vagina inhospitable to some species of bacteria such as *Staphylococcus aureus* (*S. aureus*). The low pH is a consequence of the growth of lactobacilli and their production of acidic products. Microorganisms in the vagina can also produce antimicrobial compounds such as hydrogen peroxide and bactericides directed at other bacterial species. One example is the lactocins, products of lactobacilli directed against other species of lactobacilli.

Some microbial products may affect the human host. For example, *S. aureus* can produce and excrete into its environment a variety of exoproteins including enterotoxins, Toxic Shock Syndrome Toxin-1 (TSST-1) and enzymes such as protease and lipase. *S. aureus* is found in the vagina of approximately 16% of healthy women of menstrual age. Approximately 25% of the *S. aureus* isolated from the vagina are capable of producing TSST-1.

Menstrually occurring Toxic Shock Syndrome (TSS), a severe and sometimes fatal multi-system disease, is associated with colonization by *S. aureus*. This disease has been associated with the use of tampons during menstruation. The disease is caused by TSST-1 and other staphylococcal enterotoxins.

Symptoms of TSS generally include fever, diarrhea, vomiting and a rapid drop in blood pressure. A characteristic rash is usually present. Systemic vital organ failure occurs in approximately 6% of those who contact the disease. *S. aureus* does not initiate TSS as a result of the invasion of the microorganism into the vaginal cavity. Instead as *S. aureus* grows and multiplies, it can produce TSST-1. Only after entering the bloodstream does TSST-1 act systemically and produce the symptoms attributed to TSS.

There have been numerous attempts to reduce or eliminate pathogenic microorganisms and menstrually occurring TSS by incorporating into a tampon one or more biostatic, biocidal, and/or detoxifying compounds. For example, L-ascorbic acid has been applied to a catamenial tampon to detoxify toxin found in the vagina of the human female during menstruation. Others have incorporated monoesters and diesters of polyhydric aliphatic alcohols, such as glycerol monolaurate, as detoxifying compounds. The use of other non-ionic surfactants, such as alkyl ethers, alkyl amines and alkyl amides, has also been reported as a means of avoiding the problem of degradation by esterase (see, e.g., U.S. Pat. Nos. 5,685,872; 5,618,554; and 5,612,045).

In addition to the use of certain surfactants as detoxifying compounds, surfactants have been used to treat nonwovens for many applications involving body fluids, such as menses, to enhance wicking or the ability to rapidly distribute menses in use, so as to take advantage of the absorbency of the disposable absorbent article. Prior surfactant treatments such as ethoxylated hydrocarbons, siloxanes, and ionic surfactants have been shown to aid wicking. Although such conventional surfactants may increase wettability, they often fail to effectively reduce the viscoelasticity of menses in a manner that enhances wicking to the degree of the present invention.

It has been reported that use of specific surfactants, including alkyl polyglycosides, can not only reduce the viscoelastic properties of an insult fluid, such as menses, but also can provide surfactant properties to aid in rapidly distributing the fluid. Results were reported with alkyl polyglycosides having 8–10 carbons in the alkyl chain deposited onto the fibers of the absorbent distribution layer of an absorbent product, such as a sanitary napkin. The report suggested the use of about 0.2% to about 5% of the alkyl polyglycoside based on the total weight of absorbent material.

There continues to exist a need for agents that will effectively inhibit the production of exoproteins, such as TSST-1, from Gram positive bacteria. For such agents to become widely accepted, in addition to being effective in suppressing exoprotein production, the agent(s) should desirably also be an effective aid with regard to the distribution and/or uptake of a complex fluid on the surface of a disposable absorbent article. Such agents desirably would be substantially unaffected by the enzymes lipase and esterase and would have additional desirable properties with respect to enhancement of the wetting properties of hydrophobic polymeric materials, such as, for example, nonwoven materials commonly used as covers for absorbent articles. The selection of compounds to inhibit the production of exoproteins is not so readily apparent as some compounds, such as block copolymers of propylene oxide and ethylene oxide, can stimulate toxin production by Gram positive bacteria.

SUMMARY

It has been found that alkyl polyglycoside compounds can inhibit the production of exoprotein(s) of Gram positive bacteria. Exposure to effective amounts of the alkyl polyglycoside(s) can inhibit the production of potentially harmful toxins, such as those produced by Staphylococcus and/or Streptococcal species. For example, the alkyl polyglycoside(s) can be utilized to inhibit the production of TSST-1, alpha toxin and/or enterotoxins A, B and C from *S. aureus*. The alkyl polyglycoside typically has a hydrophilic/lipophilic balance (HLB) of at least about 10 and/or an average number of carbon atoms in the alkyl chain of 8 to 12. The alkyl polyglycoside may be used alone or in combination with one or more other surfactants (e.g., myreth-3-myristate, glycerol monolaurate and/or laureth-4) and/or other additives (e.g., reducing agent(s) such as ascorbic acid, sodium bisufite, vitamin E). Such reducing agents can act as oxygen inhibiting agents and may enhance the combinations ability to reduce toxin production.

The present alkyl polyglycoside compositions are materials which, when exposed to *S. aureus* or other Gram positive bacteria in disposable absorbent articles, can reduce the production of exoproteins, such as TSST-1. It is also believed that the compounds in the present disposable absorbent articles are effective in combating the production of other types of bacterial toxins, in particular, alpha-toxin and Staphylcoccal enterotoxins A, B and C. In particular, the alkyl polyglycosides described herein are effective at inhibiting the production with respect to these aforementioned exoproteins when the compound is placed close to the outer surface of the disposable absorbent article. The alkyl polyglycoside may be used in combination with one or more other compounds, e.g., in combination with compounds such as myreth-3-myristate, glycerol monolaurate and/or laureth-4.

The present alkyl polyglycosides are particularly useful for inhibiting the production of bacterial exotoxins when incorporated into or on disposable absorbent articles. In particular, it has been found that incorporation of alkyl polyglycoside into at least the outer layer of a disposable absorbent article, such as a tampon, can be effective. The outer layer may be a cover over the absorbent material or may simply be the outer portion of the absorbent itself. For example, alkyl polyglycoside may be impregnated into the outermost layer, e.g., into an 1-2 mm thick outer layer of the absorbent material. Where the alkyl polyglycoside is present as part of a cover, the cover is commonly formed from a liquid-permeable material, such as a porous nonwoven sheet formed from fibers of a hydrophobic polymer. Of course, if desired, the absorbent article can also be formed with alkyl polyglycoside distributed throughout the absorbent material.

It has been found that use of alkyl polyglycosides not only can reduce the viscoelastic properties of a complex body fluid but can also provide surfactant properties to aid in rapidly distributing the body fluid. The alkyl polyglycoside is typically one with 8–14 carbons in the alkyl chain and is included in and/or on an outer surface of a disposable absorbent article, e.g., in an amount of at least about 3 wt. % and, desirably, at least about 6 wt. % based on the material weight of the outer layer of the product. It may be conveniently applied to the material in the form of an aqueous solution, e.g., containing from about 40 to about 60 wt. % water for example.

When employed as part of a catamenial tampon or otherwise introduced into a region affecting the vagina, the alkyl polyglycoside is desirably utilized in a manner and amount so as to minimize its effect on the natural vaginal flora. The present alkyl polyglycoside compositions are generally capable of substantially inhibiting the production of exoproteins from Gram positive bacteria (e.g., by reducing the amount of exoproteins produced by at least about 75% and, desirably, by at least about 90%) without creating a significant imbalance in the flora naturally present in the vaginal tract.

The alkyl polyglycoside compositions of the present invention may additionally include adjunct components conventionally found in pharmaceutical compositions in their art-established fashion and at their art-established levels. For example, the compositions may contain additional compatible pharmaceutical materials for combination therapy, such as supplementary antimicrobials, anti-parasitic agents, antipruritics, local anesthetics, or anti-inflammatory agents.

As used herein the term "nonwoven fabric or web" means a web having a structure of individual fibers or threads which are interlaid, but not in a regular or identifiable manner as in a knitted fabric. The term also includes individual filaments and strands, yarns or tows as well as foams and films that have been fibrillated, apertured, or otherwise treated to impart fabric-like properties. Nonwoven fabrics or webs have been formed from many processes such as for example, meltblowing processes, spunbonding processes, and bonded carded web processes. The basis weight of nonwoven fabrics is usually expressed in ounces of material per square yard ("osy") or grams per square meter ("gsm") and the fiber diameters useful are usually expressed in microns. Basis weights can be converted from osy to gsm simply by multiplying the value in osy by 33.91.

As used herein the term "microfibers" means small diameter fibers having an average diameter not greater than about 75 microns, for example, having an average diameter of from about 0.5 to about 50 microns, or more particularly, microfibers may have an average diameter of from about 2 to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as, for example, described in U.S. Pat. Nos. 4,340,563; 3,692,618; 3,802,817; 3,338,992; 3,341,394; 3,502,763; 3,502,538; and 3,542,615. Spunbond fibers are quenched and generally not tacky when deposited onto a collecting surface. Spunbond fibers are generally continuous and have average diameters frequently larger than about 7 microns, typically between about 10 and about 20 microns.

As used herein the term "meltblown fibers" means fibers formed by extruding a molten thermoplastic material through a plurality of fine, usually circular, die capillaries as molten threads or filaments into converging high velocity, usually heated, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface often while still tacky to form a web of randomly disbursed meltblown fibers. Such a process is disclosed, for example, in U.S. Pat. No. 3,849,241. Meltblown fibers are microfibers which may be continuous or discontinuous and are generally smaller than about 10 microns in average diameter.

As used herein "bonded carded webs" or "BCW" refers to nonwoven webs formed by carding processes as are known to those skilled in the art and further described, for example, in U.S. Pat. No. 4,488,928 which is incorporated herein by reference. Briefly, carding processes involve starting with a blend of, for example, staple fibers with bonding fibers or other bonding components in a bulky ball that is combed or otherwise treated to provide a generally uniform basis weight. This web is heated or otherwise treated to activate the adhesive component resulting in an integrated, usually lofty nonwoven material.

As used herein the term "polymer" generally includes but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to isotactic, syndiotactic and random symmetries.

As used herein, the term "hydrophilic" means that the polymeric material has a surface free energy such that the polymeric material is wettable by an aqueous medium, i.e., a liquid medium of which water is a major component. The term "hydrophobic" includes those materials that are not hydrophilic as defined. The phrase "naturally hydrophobic" refers to those materials that are hydrophobic in their chemical composition state without additives or treatments affecting the hydrophobicity. It will be recognized that hydrophobic materials may be treated internally or externally with surfactants and the like to render them hydrophilic.

As used herein, the term "porous hydrophobic polymer material" is meant to include any shaped article, provided it is porous and composed, in whole or in part, of a hydrophobic polymer. For example, the substrate may be a sheet-like material, such as a sheet of a foamed material. The sheet-like material also may be a fibrous web, such as a woven or nonwoven fabric or web. The substrate also may include hydrophobic polymer fibers, per se, or hydrophobic polymer fibers which have been formed into a fibrous web. The fibrous web desirably will be a nonwoven web, such as, but not limited to, a meltblown web or a spunbonded web. The substrate also may be a laminate of two or more layers of a sheet-like material. For example, the layers may be independently selected from the group consisting of meltblown webs and spunbonded webs. However, other sheet-like materials may be used in addition to, or instead of, meltblown and spunbonded webs. In addition, the layers of the laminate may be prepared from the same hydrophobic polymer or different hydrophobic polymers.

The term "hydrophobic polymer" is used herein to mean any polymer resistant to wetting, or not readily wet, by water, i.e., having a lack of affinity for water. Examples of hydrophobic polymers include, by way of illustration only, polyolefins, such as polyethylene, ethylene-propylene copolymers, and ethylene-vinyl acetate copolymers; styrene polymers, such as poly(styrene), poly(2-methylstyrene), styrene-acrylonitrile copolymers having less than about 20 mole-percent acrylonitrile, halogenated hydrocarbon polymers, such as poly (tetrafluoroethylene), tetrafluoroethylene-ethylene copolymers, poly (trifluoroethylene); vinyl polymers, such as poly (vinyl butyrate), and poly (methacrylonitrile); acrylic polymers, such as poly (n-butyl acetate), poly (ethyl acrylate), and polyesters, such as poly (ethylene terephthalate) and poly (butylene terephthalate). The hydrophobic polymer also may contain minor amounts of additives as is customary in the art. For example, the hydrophobic polymer may contain pigments, delustrants, antioxidants, antistatic agents, stabilizers, oxygen scavengers, and the like.

The term "polyolefin" is used herein to mean a polymer prepared by the addition polymerization of one or more unsaturated monomers which contain only carbon and hydrogen atoms. Examples of such polyolefins include polyethylene, polypropylene, poly (1-butene), poly (2-pentene), and the like. In addition, such term is meant to include blends of two or more polyolefins and random and block copolymers prepared from two or more different unsaturated monomers. Because of their commercial importance, the most desired polyolefins are polyethylene and polypropylene.

As already stated, the coated porous substrate may include hydrophobic polymer fibers. Such fibers are substantially uniformly coated with a hydrophilic polymeric material. As an example, the hydrophobic polymer fibers may be polyolefin fibers. For example, the polyolefin fibers may be polyethylene or polypropylene fibers. The hydrophobic polymer fibers generally may be prepared by any known means. As a practical matter, however, the fibers usually will be prepared by a melt-extrusion process and formed into a fibrous web, such as a nonwoven web. The term "melt-extrusion process" as applied to a nonwoven web is meant to include a nonwoven web prepared by any melt-extrusion process for forming a nonwoven web in which melt-extrusion to form fibers is followed by web formation, typically concurrently, on a foraminous support. The term includes, among others, such well-known processes as meltblowing, coforming, spunbonding, and the like.

As used herein, the term "pledget" means a compress used to apply pressure or press upon a body part.

The term "surface" and its plural generally refer herein to the outer or the topmost boundary of an object.

The term "durable" as used herein with reference to a coating of a hydrophilic polymeric material on the porous substrate means that the coated porous substrate remains wettable after at least three exposures to an aqueous medium, such as water, saline, and urine and other body fluids. One procedure for evaluating durability when the porous substrate is a fibrous web is a modified run-off test followed by washing and drying (a wash/dry cycle). The fibrous web typically will remain wettable for at least five cycles of exposing, washing, and drying. Desirably, the coated porous substrate will remain wettable after being subjected to at least ten cycles. The run-off test (exposure) and wash/dry procedure are described in U.S. Pat. No. 5,258,221, which is incorporated herein by reference.

As used herein, the term "hydrophilic polymeric material" means that the polymeric material has a surface free energy such that the material is wettable by an aqueous medium. That is, an aqueous medium wets the hydrophilic polymeric material with which the porous substrate is coated. For example, the surface free energy of the hydrophilic polymeric material may be at least about 50 dynes/cm. As another example, the surface free energy of the hydrophilic polymeric material may be in a range of from about 50 to about 72 dynes/cm.

The term "aqueous medium" is used herein to mean any liquid medium of which water is a major component. Thus, the term includes water per se and aqueous solutions and dispersions. For example, the aqueous medium may be a liquid bodily discharge, such as urine, menses and saliva.

As used herein, the term "wettable" and variations thereof means wettable by an aqueous medium, i.e., the aqueous medium spreads over the surface of a substrate. The term is used interchangeably with the term "wettable by water" and variations thereof and has the same meaning.

As used herein, the phrase "complex body fluid" is intended to describe a fluid generally characterized as being a viscoelastic mixture including specific components having generally inhomogeneous physical and/or chemical properties. It is the inhomogeneous properties of the specific components that often challenge the efficacy of absorbent articles in the handling of complex fluids, such as, for example, blood, menses, loose passages, nasal discharges and the like. In contrast with complex fluids, simple fluids, such as, for example, urine, physiological saline, water and the like, are generally characterized as being Newtonian and including one or more components having generally homogeneous physical and/or chemical properties. As a result of having homogeneous properties, the one or more components of simple fluids behave substantially similarly during absorption or adsorption.

As used herein, the phrase "absorbent article" refers to devices which absorb and contain body fluids, and more specifically, refers to devices which are placed against or near the skin to absorb and contain the various fluids discharged from the body. The term "disposable" is used herein to describe absorbent articles that are not intended to be laundered or otherwise restored or reused as an absorbent article after a single use. Examples of such disposable absorbent articles include, but are not limited to: health care related products including bandages and tampons such as those intended for medical, dental, surgical and/or nasal use; personal care absorbent products such as feminine hygiene products (e.g., sanitary napkins, panty liners and catamenial tampons), diapers, training pants, incontinent products and the like, wherein the inhibition of the production of exoproteins from Gram positive bacteria would be beneficial.

DETAILED DESCRIPTION

Figure 1:
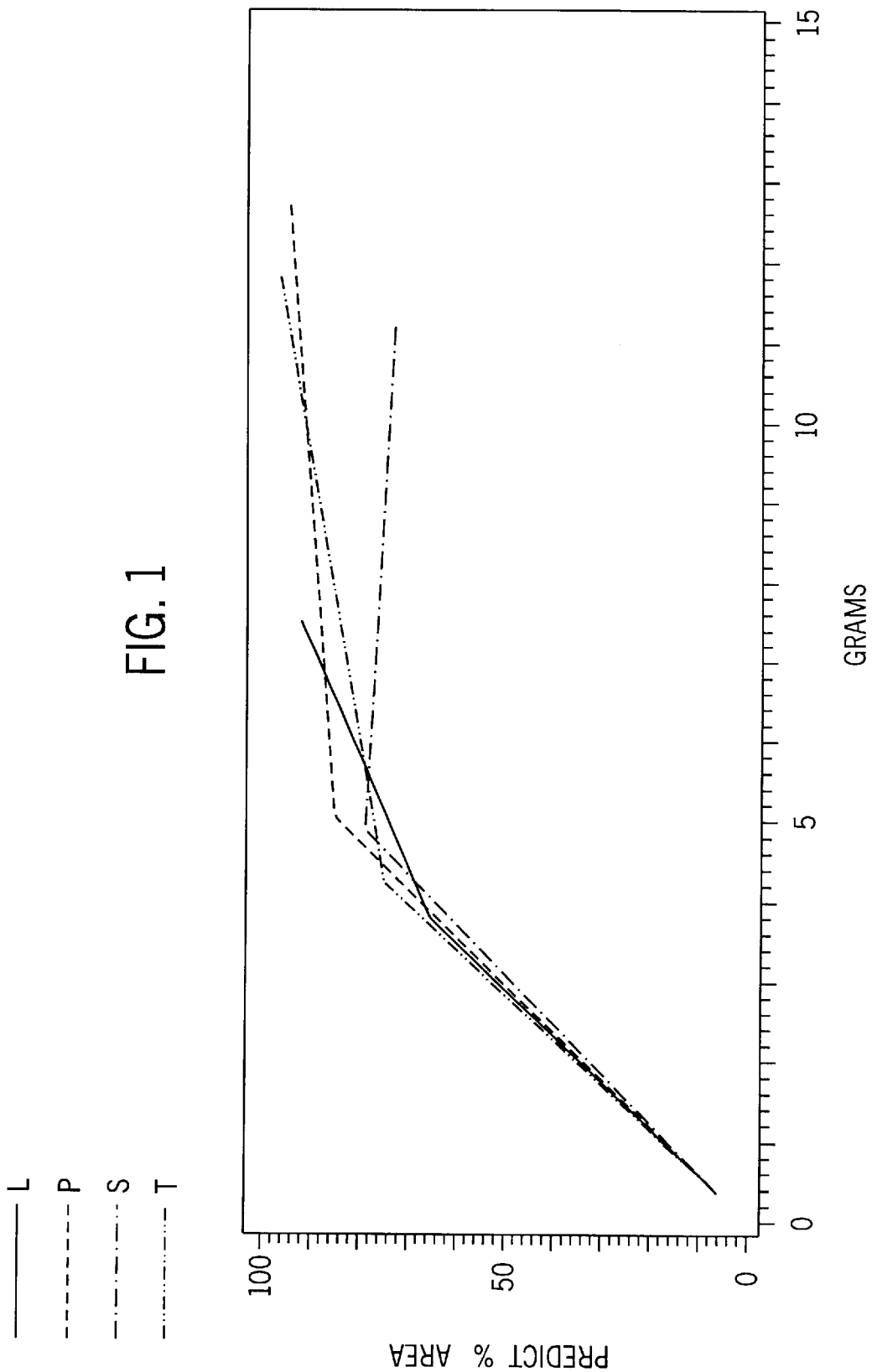
FIG. 1 is a graph showing the predicted percent stain area as a function of grams loaded for the internal stain pattern for tampon prototypes with covers coated with various surface treatments. The codes for the graph correspond to the following treatments of the cover used to form the tampon protoptypes: L—7 wt. % Laureth-4; P—18 wt. % PPG-5 Laureth-5; S—8 wt. % Steareth-2; and T—14 wt. % Glucopon 220.

Disposable absorbent articles suitable for use in the present invention are particularly adapted to receive simple and/or complex body fluids. For purposes of discussion, the absorbent article specifically discussed herein is a catamenial tampon. However, it would be readily understood by persons skilled in the art that the present invention may also be applied to other disposable absorbent articles wherein inhibition of exoproteins from Gram positive bacteria would be beneficial.

Specifically, catamenial tampons suitable for use in the present invention include an absorbent. The absorbent can be formed from fibers which are assembled into an absorbent sheet or ribbon. Alternatively, the absorbent can be formed from absorbent fibers which are assembled and compressed into a generally elongated and/or cylindrical configuration. The absorbent is desirably formed from cellulosic fibers, such as cotton and rayon. For example, the absorbent can be 100% cotton, 100% rayon, a blend of cotton and rayon fibers, or other materials known to be suitable for tampons.

The absorbent, when formed from an absorbent sheet or ribbon, is often constructed from a blend of cotton and rayon fibers. Two processes for forming such an absorbent sheet are known as "carding" and "airlaying." Depending upon the desired absorbency one desires in the finished tampon, the basis weight of the absorbent sheet can vary. The U.S. Food and Drug Administration (FDA) has set absorbency standards for "junior," "regular," "super" and "super-plus__" size tampons. In order to meet the FDA standards for these four sizes, the absorbent sheets are targeted to have basis weights of about 100 grams per square meter (gsm), about 120 gsm, about 170 gsm and about 230 gsm, respectively. Typically, the carding process is controlled to produce an absorbent sheet with a width of between about 40 to about 60 mm, desirably about 50 mm. The basis weight and/or the length of the absorbent can also be adjusted to form the different size tampons.

The absorbent can be partially or fully enclosed by a cover. Desirably, the cover is liquid-permeable. By "liquid-permeable" it is meant that liquids, such as water or body fluid, are able to pass through the cover. The cover can be hydrophilic or hydrophobic. By "hydrophilic" it is meant that the cover has an affinity for absorbing or tending to combine with water. By "hydrophobic" it is meant the cover is antagonistic to or tending not to combine with water. The cover can also be treated with a surfactant or other material to make it hydrophilic or to make it more hydrophilic. The cover desirably includes the alkyl polyglycoside disposed thereon so as to contact the body fluid the absorbent article is designed to receive.

The liquid-permeable cover can be formed from woven or nonwoven materials having a porous substrate. Woven materials include textile fabrics which can be made from rayon, cotton or polyolefins. The polyolefins can be either staple or continuous filaments. The nonwoven materials can include spunbond, bonded carded webs and hydroentangled webs. Spunbond and bonded carded webs are commercially sold by Kimberly-Clark Corporation having an office at 401 N. Lake St., Neenah, Wis. 54957. Another nonwoven material which can be used as the cover is formed from 100% polyester fibers held together by a binder. This material is known as powder-bonded-carded web (PBCW). PBCW is commercially available from HDK Industries, Inc., having an office at 304 Arcadia Dr., Greenville, S.C. 29609. The cover can further be formed from an apertured thermoplastic film having either a two-dimensional or three-dimensional thickness. Apertured thermoplastic films are available from several commercial vendors. Two such vendors include Pantex Srl, Pantex Sud Srl, Via Terracini snc. having an office at 51031 Agliana, Pistoia,ltaly, and Applied Extrusion Technology having a mailing address of P.O. Box 582, Middleton, Del. 19709.

Even though the cover may be formed predominantly from a hydrophobic polymeric material, e.g., a porous nonwoven sheet formed from fibers of hydrophobic polymer, treatment of the surface of the cover with alkyl polyglycoside can render the surface wettable with aqueous fluids. One example of a particularly suitable cover material is a spunbond formed from a hydrophobic polymer such as polypropylene or polyethylene. Such a cover material typically has a basis weight of about 0.1 to about 0.8 osy and includes sufficient alkyl polyglycoside to render the surface of the cover wettable with an aqueous fluid. The alkyl polyglycoside is generally present as a durable coating on the surface of fibers which make up the cover, i.e., the porous substrate remains wettable after at least three exposures to an aqueous medium, such as water, saline, urine or other body fluids. In addition, the alkyl polyglycoside is desirably selected so that a sufficient amount can inhibit the production of exoproteins, such as TSST-1, from Gram positive bacteria. This can be achieved, for example, by coating a porous polypropylene spunbond sheet with an alkyl polyglycoside having an HLB of about 12 to about 15.

The present alkyl polyglycoside-containing absorbent articles, when exposed to *S. aureus* or other Gram positive bacteria, can reduce the production of potentially harmful exoproteins. In particular, exposure to the alkyl polyglycoside(s) can inhibit the production of potentially harmful proteins produced by Staphylococcus and/or Streptococcal species.

The alkyl polyglycoside is generally present in at least about 3 wt. % and more typically about 6 to about 10 wt. % add-on (based on the weight of the spunbond substrate). In some instances, it may be useful to employ higher levels of the alkyl polyglycoside, e.g., up to about 20 wt. % (add-on). As used herein, the term "add-on wt. %" refers to the amount of alkyl polyglycoside employed as a percentage of the dry weight of the uncoated substrate. Thus, 10 wt. % (add-on) is equal to 9.1 wt. % based on the total weight of the coated substrate (10/110=9.1). Unless otherwise explicitly stated herein, all amounts of alkyl polyglycoside on a substrate (absorbent or non-absorbent) are stated in terms of add-on wt. %, even though the amount may simply be referred to as "wt. %". This is not the case for amounts of alkyl polyglycoside present as part of a fluid composition, where the amounts are stated either in mmolar or %(w/v) as a percentage of the total composition. The amount of alkyl polyglycoside used in a specific absorbent article will depend upon the particular form and use of the article. The amount of alkyl polyglycoside used in a specific application will depend upon the particular form and/or use of the composition or article. The actual amount can be readily selected by those skilled in the art based on the teaching of this application. For example, a catamenial tampon designed to be inserted into a body cavity and subsequently in intimate contact with the vaginal epithelium may require substantially less alkyl polyglycoside than an absorbent article worn exterior to the body.

The alkyl polyglycoside can generally be represented by the formula:

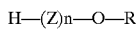

where "Z" is a saccharide residue having 5 or 6 carbon atoms, "n" is a number having a value between about 1 and about 6, and "R" represents an alkyl group, typically having 8 to 18 carbon atoms. Commercially available examples of suitable alkyl polyglycosides include Glucopon 220, 225, 425, 600 and 625, all available from Henkel Corporation. These products are all mixtures of alkyl mono- and oligoglucopyranosides with alkyl groups based on fatty alcohols derived from coconut and/or palm kernel oil. Glucopon 220, 225 and 425 are examples of particularly suitable alkyl polyglycosides. Glucopon 220 is an alkyl polyglycoside which contains an average of 1.4 glucosyl residues per molecule and a mixture of 8 and 10 carbon alkyl groups (average carbons per alkyl chain—9. 1). Glucopon 225 is a related alkyl polyglycoside with linear alkyl groups having 8 or 10 carbon atoms (average alkyl chain—9.1 carbon atoms) in the alkyl chain. Glucopon 425 includes a mixture of alkyl polyglycosides which individually include an alkyl group with 8, 10, 12, 14 or 16 carbon atoms (average alkyl chain—10.3 carbon atoms). Glucopon 600 includes a mixture of alkyl polyglycosides which individually include an alkyl group with 12, 14 or 16 carbon atoms (average alkyl chain 12.8 carbon atoms). Glucopon 625 includes a mixture of alkyl polyglycosides which individually include an alkyl group having 12, 14 or 18 carbon atoms (average alkyl chain 12.8 carbon atoms). Another example of a suitable commercially available alkyl polyglycoside is TL 2141, a Glucopon 220 analog available from ICI.

It will be understood that as referred to herein, an "alkyl polyglycoside" may consist of a single type of alkyl polyglycoside molecule or, as is typically the case, may include a mixture of different alkyl polyglycoside molecules. The different alkyl polyglycoside molecules may be isomeric and/or may be alkyl polyglycoside molecules with differing alkyl groups and/or saccharide portions. By use of the term "alkyl polyglycoside isomers," reference is made to alkyl polyglycosides which, although including the same alkyl ether residues, may vary with respect to the location of the alkyl ether residue in the alkyl polyglycoside as well as isomers which differ with respect to the orientation of the functional groups about one or more chiral centers in the molecules. For example, an alkyl polyglycoside can include a mixture of molecules with saccharide portions which are mono-, di- or oligosaccharides derived from more than one 6 carbon saccharide residue and where the mono-, di- or oligosaccharide has been etherified by reaction with a mixture of fatty alcohols of varying carbon chain length. The present alkyl polyglycosides desirably include alkyl groups where the average number of carbon atoms in the alkyl chain is 9 to 11. One example of a suitable alkyl polyglycoside is a mixture of alkyl polyglycoside molecules with alkyl chains having 8 to 10 carbon atoms.

The alkyl polyglycosides employed in the absorbent article described herein can be characterized in terms of their HLB. This can be calculated based on their chemical structure using techniques well known to those skilled in the art. The HLB of the alkyl polyglycosides used in the present methods typically falls within the range of about 10 to 5 about 15. Desirably, the present alkyl polyglycosides have an HLB of at least about 12 and, more desirably, about 12 to about 14.

In one embodiment of the present invention, an absorbent article includes a liquid-permeable cover which typically contains at least about 3 wt. %, generally no more than about 20 wt. % and, more desirably, about 6 to about 10 wt. % alkyl polyglycoside. A suitable example of such an absorbent article is a catamenial tampon having a liquid-permeable cover which includes the alkyl polyglycoside. Typically, such a tampon would have a cover formed from spunbond fibers of a hydrophobic polymeric material, e.g., a spunbond polypropylene cover, with the alkyl polyglycoside coated on the outside of the fibers.

The fibers from which the present absorbent articles are made may be produced, for example, by the meltblowing or spunbonding processes, including those producing bicomponent, biconstituent or polymer blend fibers which are well known in the art. These processes generally use an extruder to supply melted thermoplastic polymer to a spinneret where the polymer is fiberized to yield fibers which may be staple length or longer. The fibers are then drawn, usually pneumatically, and deposited on a moving foraminous mat or belt to form the nonwoven fabric. The fibers produced in the spunbond and meltblown processes are typically microfibers as defined above. The manufacture of spunbond and meltblown webs is discussed generally above.

As mentioned, the nonwoven also may be a bonded carded web. Bonded carded webs are made from staple fibers, which are usually purchased in bales. The bales are placed in a picker, which separates the fibers. Then, the fibers are sent through a combing or carding unit, which further breaks apart and aligns the staple fibers in the machine direction to form a generally machine direction-oriented fibrous nonwoven web. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable bonding method, particularly when using bicomponent staple fibers, is through-air bonding.

The present absorbent articles contain an effective amount of the inhibiting alkyl polyglycoside compound to substantially inhibit the formation of exoproteins such as TSST-1 when the absorbent article such as a catamenial tampon or sanitary napkin, is exposed to Gram positive bacteria. Where the alkyl polyglycoside is present as part of an absorbent of an absorbent article, at least about 0.005 millimoles of alkyl polyglycoside compound per gram of absorbent may be effective for reducing exoprotein production.

A material suitable for use as an absorbent in the absorbent articles described herein is a nonwoven web composed of about 3 denier polyethylene 5 sheath/polypropylene core bicomponent staple fibers having a length of about 38 mm. Such bicomponent fibers can be obtained from Chisso Corporation and are typically supplied with a vendor fiber finish. The staple fibers can be sent through an opener and uniformly mixed together before being carded into a web at a line speed of about 15 meters per minute (about 50 feet per minute). Once the web is formed, it can be sent through a through-air bonder (drum type) with an air temperature of approximately 131° C. Typical dwell times within the bonder are between about 3 and about 4.5 seconds. The resultant web, which has a basis weight of about 100 gsm and a density of about 0.06 gm/cm$^3$, can then be wound up on a roll.

Other materials suitable for use as an absorbent include materials which include hydrophilic natural and/or synthetic fibers. For example, a material formed from a mixture of cotton and rayon fibers is an absorbent material that can be used to form all or a portion of the absorbent of an absorbent article such as a catamenial tampon and a sanitary napkin.

The alkyl polyglycoside treating composition used to form the present absorbent articles may contain other additives as appropriate for the desired result so long as they do not have a major detrimental effect on the activity of the alkyl polyglycoside. Examples of such additives include additional conventional surfactants such as ethoxylated hydrocarbons or ionic surfactants, or co-wetting aids such as low molecular weight alcohols. As mentioned, the composition is desirably applied from high solids, advantageously about 80% or less solvent or water, so as to minimize drying and its attendant costs and deleterious effects. The treating composition may be applied in varying amounts depending on the desired results and application. For sanitary napkin distribution layer applications, for example, effective results are obtained within a range of about 5 to about 20% solids add-on based on the dry weight of the fabric, with a range of about 6 to 10% being desirable from the perspective of both cost and performance. Also, as will be recognized by those skilled in this art, many substrate materials may be treated in accordance with the invention including nonwovens such as spunbond, meltblown, carded webs and others as well as woven webs and even films and the like where improved fluid distribution is desired. It will also be recognized by those skilled in this art that some alkyl polyglycoside may be used as internal additives, that is, added to the polymer melt directly or in a concentrate form. After fiber formation, such additives can migrate to the fiber surface and impart the desired effect. For further discussion of internal addition of additives, see for example, U.S. Pat. No. 5,540,979, the contents of which are incorporated herein by reference.

The compositions may be applied to an absorbent article using conventional methods for applying an inhibitory agent to the desired absorbent article. For example, catamenial tampons without a cover, may be dipped directly into a liquid bath having the composite and then can be air dried, if necessary, to remove any volatile solvents. For compressed tampons, impregnating any of its elements is best done before compressing. The compositions when incorporated on and/or into the tampon may be fugitive, loosely adhered, bound, or any combination thereof. As used herein the term "fugitive" means that the composition is capable of migrating through the tampon materials. For example, the alkyl polyglycoside may be blended together with a polymeric material that is to be processed into a component of an absorbent article.

Alternatively, an alkyl polyglycoside containing solution may be applied directly onto an individual layer of material before it is incorporated into an article to be manufactured, such as an absorbent article. For example, an aqueous solution containing the alkyl polyglycoside can be sprayed onto the surface of a liquid-permeable cover or absorbent material designed to be incorporated into an absorbent article. This can be done either during the production of the material or during a fabrication process which incorporates the material into the absorbent article being manufactured.

Nonwoven webs coated with alkyl polyglycoside can be prepared by conventional processes. For example, alkyl polyglycoside can be applied to one or both sides of a traveling web. It will be appreciated by those skilled in the art that the application can be carried out as an inline treatment or as a separate, offline treatment step. A web, such as a spunbond or meltblown nonwoven, can be directed over support rolls to a treating station including rotary spray heads for application to one side of the web. An optional treating station may include rotary spray heads to apply to alkyl polyglycoside to the opposite side of the web. Each treatment station generally receives a supply of treating liquid from a reservoir. The treated web may then be dried if needed by passing over dryer cans or other drying means and then be wound as a roll or converted to the use for which it is intended. Alternative drying apparatus such as ovens, through air dryers, infra red dryers, air blowers, and the like may also be utilized.

One example of a representative absorbent article is a catamenial tampon which includes alkyl polyglycoside. The alkyl polyglycoside may be incorporated into the absorbent of the tampon and/or on or in a cover. Tampons with an alkyl polyglycoside, such as Glucopon 220, deposited on the cover are particularly suitable for inhibiting the production of bacterial exoproteins by Gram positive bacteria such as S. aureus.

The inhibitory alkyl polyglycoside composition may additionally employ one or more conventional pharmaceutically-acceptable and compatible carrier materials useful for the desired application. The carrier can be capable of co-dissolving or suspending the materials used in the composition. Carrier materials suitable for use in the instant composition, therefore, include those well-known for use in the cosmetic and medical arts as a basis for ointments, lotions, creams, salves, aerosols, suppositories, gels and the like. A suitable carrier can be comprised of alcohols and surfactants.

The following examples are presented to illustrate the present invention and to assist one of ordinary skill in making and using the same. The examples are not intended in any way to otherwise limit the scope of the invention.

EXAMPLES

Example A

The effect of Glucopon 220 on growth of *S aureus* and production of TSST-1 was examined by placing the desired concentration, expressed in millimoles/milliliter (millimolar hereinafter mM), in 100 mL of a growth medium in a sterile, 500 mL Corning fleaker™.

The growth medium was prepared as follows: 37 grams of brain heart infusion broth (BHI) was dissolved in 880 mL distilled water and sterilized. BHI broth is available from Difco™ Laboratories, Becton Dickinson Microbiology Systems, Cockeysville, Md. 21030-0243.The BHI was supplemented with 100 mL fetal bovine serum (FBS) available from Sigma Chemical Company, P.O. Box 14508, St Louis, Mo. 63178-9916. Ten mL of a 0.021 molar sterile solution of the hexahydrate of magnesium chloride (Sigma Chemical Company) was added to the BHI-FBS mixture. Ten mL of a 0.027 molar sterile solution of L-glutamine (Sigma Chemical Company) was also added to the BHI-FBS mixture.

Glucopon 220 was added directly to the growth medium, sterilized, and diluted in sterile growth medium to obtain the desired final concentrations.

In preparation for inoculation of the fleakers of growth medium containing Glucopon 220, an inoculating broth was prepared as follows: *S aureus* MN8 was streaked onto a tryptic soy agar plate (TSA; Difco Laboratories) and incubated at 35° C. The test organism in this example was obtained from Dr. Pat Schlievert, Department of Microbiology, University of Minnesota Medical School, Minneapolis, Minn. After 24 hours of incubation three to five individual colonies were picked with a sterile inoculating loop and used to inoculate the 10 mL of growth medium. The tube of inoculated growth medium was incubated at 35° C. in atmospheric air. After 24 hours of incubation, the culture was removed from the incubator and mixed well on a S/P brand vortex mixer. A second tube containing 10 mL of the growth medium was inoculated with 0.5 mL of the above 24 hour old culture and incubated at 35° C. in atmospheric air. After 24 hours of incubation the culture was removed from the incubator and mixed well on a S/P brand vortex mixer. The optical density of the culture fluid was determined in a microplate reader (Bio-Tek Instruments, Model EL309, Box 998, Winooski, Vt. 05404-0998). The amount of inoculum necessary to give $5\times10^6$ CFU/mL was determined using a previously prepared standard curve.

The experiment included fleakers of growth medium without Glucopon 220 (control) or with varying concentrations of Glucopon 220. Each fleaker was inoculated with the amount of inoculum determined as described above. The fleakers were capped with sterile aluminum foil and incubated at 35° C. in atmospheric air in a Lab-Line orbital water bath at 180 rpm. The Lab-Line bath was obtained from VWR Scientific Products, 1430 Waukegan Road, McGaw Park, Ill. 60085. Five milliliter samples were removed at the desired time points and the optical density of the culture fluid was determined. The culture fluid was assayed for the number of colony forming units of *S aureus* using standard plate count procedures.

After 24 hours of incubation, the experiment was repeated using fresh medium. However, in this instance, the inoculum was from the 24-hour old fleaker containing the same concentration of Glucopon 220. The method described above for determining the amount of fluid necessary to obtain a $5\times10^6$ CFU/mL inoculum was used. For example, *S. aureus* grown in 2 mM Glucopon 220 were inoculated into fresh growth medium containing 2 mM Glucopon 220. Glucopon 220 was tested at 20, 10, 4, 2, 1, and 0.5 mM concentrations. No growth was observed in the presence of the 10 and 20 mM concentrations. Growth was not observed in the growth medium containing 4 mM Glucopon 220 until 26 hours after inoculation, thus it was not reinoculated into fresh medium after the first 24 hours of incubation.

Five milliliters of the remaining culture fluid was prepared for the analysis of TSST-1 as follows: the culture fluid was centrifuged at 2500 rpm at 2–10° C. for 15 minutes. The supernatant was filter sterilized through an Autovial® 5 syringeless filter, 0.2 $\mu$M pore size (Whatman, Inc., Clifton, N.J.). The resulting fluid was frozen at −70° C. in a Fisherbrand® 12×75 mm polystyrene culture tube, Fisher Scientific, 585 Alpha Drive, Pittsburgh, Pa. 15328.

The amount of TSST-1 per mL was determined by a non-competitive, sandwich enzyme-linked immunoabsorbent assay (ELISA). Samples of the culture fluid and the TSST-1 reference standard were assayed in triplicate. The method employed was as follows: four reagents, rabbit polyclonal anti-TSST-1 IgG (LTI-101), rabbit polyclonal anti-TSST-1 IgG conjugated to horseradish peroxidase (#LTC-101), TSST-1 (#TT-606), and normal rabbit serum (NRS) certified anti-TSST-1 free (#NRS-10) were purchased from Toxin Technology, Inc., 7165 Curtiss Avenue, Sarasota, Fla. 34231. A 10 ug/mL solution of the polyclonal rabbit anti-TSST-1 IgG was prepared in phosphate buffered saline (PBS), pH 7.4. The PBS was prepared from 0.016 molar $NaH_2PO_4$, 0.004 molar $NaH_2PO_4$-$H_2O$, 0.003 molar KCl and 0.137 molar NaCl, all available from Sigma Chemical Company. One hundred microliters of the polyclonal rabbit anti-TSST-1 IgG solution was pipetted into the inner wells of polystyrene microplates, catalogue #439454, obtained from Nunc-Denmark. The plates were covered and incubated at room temperature overnight. Unbound anti-toxin was removed by draining until dry.

TSST-1 was diluted to 10 ng/mL in PBS with phosphate buffered saline (pH 7.4) containing 0.05% (vol/vol) Tween-20 (PBS-Tween) available from Sigma Chemical Company and 1% NRS (vol/vol) and incubated at 4° C. overnight. Test samples were combined with 1% NRS (vol/vol) and incubated at 4° C. overnight.

One hundred microliters of a 1% (wt/vol) solution of the sodium salt of casein in PBS (Sigma Chemical Company) was pipetted into the inner wells of polystyrene microplates, the plates were covered, and incubated at 35° C. for one hour. Unbound BSA was removed by 3 washes with PBS-Tween. TSST-1 reference standard (10 ng/mL) treated with NRS, test samples treated with NRS, and reagent controls were pipetted in 200 microliter volumes to their respective wells on the first and seventh columns of the plate. One hundred microliters of PBS-Tween was added to the remaining wells. The TSST-1 reference standard and test samples were then serially diluted 5 times in the PBS-Tween by transferring 100 microliters from well-to-well. The samples were mixed prior to transfer by repeated aspiration and expression. This was followed by incubation for 1.5 hours at 35° C. and five washes with PBS-T and three washes with distilled water to remove unbound toxin.

The rabbit polyclonal anti-TSST-1 IgG conjugated to horseradish peroxidase was diluted according to manufacturer's instructions and 50 microliters was added to each microtiter well, except well A-1, the conjugate control well. The plates were covered and incubated at 35° C. for one hour.

Following incubation, the plates were washed five times in PBS-Tween and three times with distilled water. Following the washes, the wells were treated with 100 microliters of a horseradish peroxidase substrate buffer consisting of 5 mg of o-phenylenediamine and 5 microliters of 30% hydrogen peroxide (both from Sigma Chemical Company) in 11 mL of citrate buffer, pH 5.5. The citrate buffer was prepared from 0.012 anhydrous citric acid and 0.026 molar dibasic sodium phosphate both available from Sigma Chemical Company. The plates were incubated for 15 minutes at 35° C. The reaction was stopped by the addition of 50 microliters of a 5% sulfuric acid solution. The intensity of the color reaction in each well was evaluated using the BioTek Model EL309 microplate reader (OD 490 nm). TSST-1 concentrations in test samples were determined from the reference toxin regression equation derived during each assay procedure.

The efficacy of Glucopon 220 in inhibiting the production of TSST-1 is shown in Table I below. The data is presented in units of TSST-1 (ng/OD units) as well as showing the TSST-1 levels as a percentage of the untreated control.

TABLE I

| Glucopon 220 (mM) | OD (10 hr) | TSST-1 (ng/OD units) | TSST-1 (% of control) | OD (24 hr) | TSST-1 (ng/OD units) | TSST-1 (% of control) |
|---|---|---|---|---|---|---|
| First 24 hour incubation | | | | | | |
| None | 7.49 | 189 | — | 11.47 | 1471 | — |
| 4 mM | 0.03 | ND | — | 0.04 | ND | — |
| 2 mM | 7.95 | 23 | 12% | 11.47 | 37 | 3% |
| 1 mM | 8.1 | 63 | 33% | 11.21 | 168 | 11% |
| 0.5 mM | 7.45 | 143 | 76% | 10.71 | 187 | 13% |
| Second 24 hour incubation in fresh medium | | | | | | |
| None | 6.34 | 232 | — | 10.00 | 1141 | — |
| 2 mM | 7.91 | 12 | 8% | 11.93 | 37 | 3% |
| 1 mM | 6.89 | 41 | 17% | 9.92 | 127 | 11% |

Example B

Tampon prototypes with covers treated with a variety of different non-ionic surface treatments were examined in a laboratory microbial challenge test to determine the effect surface treatments on TSST-1 production by *Staphylococcus aureus*.

Cover material was produced by coating the particular non-ionic surface treatment onto a commercially produced 0.4 osy polypropylene spunbond cover material. The surface treatment was applied by diluting the surfactant to the desired concentration with purified water and applying the solution to the nonwoven cover material with a Butterworth treater. The amount of solution applied was controlled by nip pressure and line speed.

The coated cover was used to fabricate tampon prototypes containing an absorbent layer made up of a mixture of cotton and rayon fibers. An uncompressed absorbent pledget made of the combination of cotton and rayon fibers was covered with the treated spunbond cover material. A string hole was punched through the uncompressed pledget. A string was knotted and looped through the absorbent pledget and cover and the resulting construction was compressed and placed in a tampon applicator.

The add-on level of the various cover surface treatments was determined by the weight of extractables. Correction was made for the level of extractables obtained from untreated cover material, extraction efficiency for the particular surfactant and the solids content of the surfactants. The treated spunbond covers were sampled in triplicate and the recovery efficiency was calculated from triplicate testing of one add-on level for each surfactant. As controls, spiked samples were prepared using untreated nonwoven cover material and reference samples of the various surfactants. The spiked samples were subjected to the same extraction conditions as the corresponding coated cover materials.

Tampon prototypes to be tested were randomly selected from each of the groups of protoypes with varying types of cover coating. The prototypes were grasped with sterile forceps. The string was cut off with sterile scissors, and the pledget placed into a sterile, capped polystyrene test tube with the string end down.

Each pledget was inoculated with 10.5 mL of an inoculating broth containing $5 \times 10^6$ CFU/mL of *S. aureus* MN8 (obtained from Dr. Pat Schlievert, Department of Microbiology, University of Minnesota Medical School, Minneapolis, Minn.). After incubation at 35° C. for 24 hours in plugged tubes, the pledgets were placed into sterile stomacher bags and sterile fluid was added. The pledgets and fluid were then stomached. Using sterile technique, aliquots of fluid were removed from the stomacher bag and placed into sterile tubes for testing.

Plate count samples were prepared by vortexing the sample, withdrawing 5 mL sample and placing the 5 mL in a fresh, sterile 50 mL centrifuge tube. The sample was then sonicated in a Virtis Virsonic 475 Sonicator for 15 seconds at 8% output power. When all samples were sonicated, the number of colony forming units per mL were determined using standard plate count procedures.

Assay for TSST-1 Concentration

Five milliliters of the culture fluid was prepared for the analysis of TSST-1 as follows: the culture fluid was centrifuged at 9000 rpm at 4° C. for 5 minutes. The supernatant was filter sterilized through 0.45 micron filter and frozen at −70° C. in two aliquots in 1.5 mL polypropylene screw cap freezer vials.

The amount of TSST-1 per mL was determined by a non-competitive, sandwich enzyme-linked immunoabsorbent assay (ELISA). Samples of the culture fluid and the TSST-1 reference standard were assayed in triplicate. The method employed was as follows: four reagents, rabbit polyclonal anti-TSST-1 IgG (LTI-101), rabbit polyclonal anti-TSST-1 IgG conjugated to horseradish peroxidase (#LTC-101), TSST-1 (#TT-606), and normal rabbit serum (NRS) certified anti-TSST-1 free (#NRS-10) were purchased from Toxin Technology, Inc., 7165 Curtiss Avenue, Sarasota, Fla. 34231. Sixty-two microliters of polyclonal rabbit anti-TSST-1 IgG (#LTI-101) was appropriately diluted so that a 1:100 dilution gave an absorbance of 0.4 at 205 nanometers. This was added to 6.5 mL of 0.5 molar carbonate buffer, pH 9.6, and 100 ul of the solution was pipetted into the inner wells of polystyrene microplates, catalogue #439454, obtained from Nunc-Denmark. The plates were covered and incubated at 37° C. overnight. Unbound anti-toxin was removed by four washes with phosphate buffered saline (pH 7.2) (0.016 molar $NaH_2PO_4$ and 0.9% [wt/vol] NaCl both available from Sigma Chemical Company) containing 0.5% [vol/vol] Tween 20 (PBS-Tween), also available from Sigma Chemical Company in an automatic plate washer. The plates were treated with 100 ul of a 1% [wt/vol] solution of bovine serum albumin (BSA), fraction V, in the 0.5 molar carbonate buffer described above. BSA fraction V is available from Sigma Chemical Company. The plates were covered and incubated at 37° C. for one hour. Unbound BSA was removed by six washes with 250 ul PBS-Tween. Test samples were treated with normal rabbit serum (10% [vol/vol] final concentration) for 15 minutes at room temperature. TSST-1 reference standard, serially diluted from 1–20 ng/mL in PBS-Tween and the NRS treated test samples (serially diluted in PBS-Tween so that the resultant TSST-1 concentration is between 1–20 ng), were pipetted in 100 ul volumes to their respective wells. This was followed by incubation for two hours at 37° C. and four washes of 250 mL PBS-Tween to remove unbound toxin. The rabbit polyclonal anti-TSST-1 IgG conjugated to horseradish peroxidase was diluted according to manufacturer's instructions. The final use dilution of the conjugate was determined by running standard curves of TSST-1 reference standard with the conjugate at undiluted, 1:2 and 1:4 dilutions. The dilution that gave results most comparable to previous lots of conjugate was selected. One hundred microliter volumes of this dilution was added to each microtiter well. The plates were covered and incubated at 37° C. for one hour.

Following incubation the plates were washed six times in 250 ul PBS-Tween and three times with distilled water. Following the washes, the wells were treated with 100 ul of a horseradish peroxidase substrate solution consisting of 0.015 molar sodium citrate (pH 4.0), 0.6 millimolar 2,2'-Azino-bis-(3-ethylbenzthiazoline-6-sulfonic acid) diammonium salt and 0.009% (vol/vol) hydrogen peroxide, all available from Sigma Chemical Company. The intensity of the color reaction in each well was evaluated over time using a BioTek Model EL340 Microplate reader (OD 405 nm) and Kineticalc® software available from Biotek Instruments, Inc. TSST-1 concentrations in test samples derived from the reference toxin regression equations for each assay procedure.

The efficacy of Glucopon 220 in inhibiting the production of TSST-1 is shown in Table II below.

TABLE II

| Surface Treatment | Amount (Wt. % Solids) | TSST-1 (ng/mL) | Final [S. aureus] (× $10^9$ CFU/ml) |
|---|---|---|---|
| Laureth-4 | 7 wt. % | 531.8 | 4.57 |
| PPG-5 Laureth-5 | 18 wt. % | 609.2 | 3.82 |
| Glucopon 220 | 3 wt. % | 554.8 | 6.41 |
| Glucopon 220 | 14 wt. % | 327.5 | 6.99 |
| Steareth-2 | 8 wt. % | 680.7 | 5.76 |

Example C

Intake Data

Cover material similar to that used to produce a tampon was prepared by coating a solution containing the designated amount (on a solids basis) of the chosen non-ionic surface treatment onto a polypropylene spunbond web (0.4 osy). The solutions were prepared with HPLC grade water except in the case of Steareth-2 which was dissolved in HPLC grade water containing 3 wt. % hexanol. The spunbond material was coated at a line speed of 75 fpm. The sample was then dried (dry can temperature−225° F.) before use and cut into four or eight inch lengths. Table III below shows the concentrations of the solutions, wet pick up levels and nip pressures used to coat the spunbond cover material with the various surface treatments.

TABLE III

| Surfactant | Target Wet Pick Up (wt. %) | Nip Pressure |
|---|---|---|
| 3% Glucopon 220 | 100% | 7 psi |
| 12% Glucopon 220 | 100% | 8 psi |
| 9% Laureth-4 | 100% | 8 psi |
| 8.7% PPG-5 Laureth-5 | 150% | 4 psi |
| 3% Steareth-2 | 200% | 3 psi |

An absorbent ribbon formed from a blend of ⅔ rayon and ⅓ cotton fibers was prepared and cut into 4 inch lengths. Four inch lengths of the treated spunbond web were placed over a 4 inch piece of the rayon/cotton absorbent. Each sample was than subjected to three insults of 0.25 mL of a low viscosity menses simulant similar to that described in International Patent Application WO 98/09662. The insults were delivered at a rate of 2.5 mL/min at intervals of three minutes. The intake time (in seconds) for the simulated menses to pass into the cover sample was recorded for each insult. The results are shown in Table IV below.

TABLE IV

| Surfactant | Conc. (wt. %) | Intake Time (sec) First | Second | Third |
|---|---|---|---|---|
| Glucopon 220 | 3% | 6.97 | 8.87 | 10.84 |
| Glucopon 220 | 6% | 6.85 | 8.73 | 9.70 |

TABLE IV-continued

| Surfactant | Conc. (wt. %) | Intake Time (sec) | | |
|---|---|---|---|---|
| | | First | Second | Third |
| Glucopon 220 | 9% | 6.78 | 7.78 | 8.13 |
| Glucopon 220 | 13% | 6.90 | 7.95 | 8.23 |
| Laureth-4 | 3% | 6.71 | 7.74 | 8.27 |
| Laureth-4 | 6% | 6.82 | 8.01 | 8.56 |
| Laureth-4 | 9% | 6.51 | 7.27 | 7.59 |
| Laureth-4 | 13% | 6.51 | 7.46 | 7.97 |
| PPG-5 Laureth-5 | 3% | 6.53 | 7.47 | 7.93 |
| PPG-5 Laureth-5 | 6% | 6.84 | 8.18 | 8.84 |
| PPG-5 Laureth-5 | 9% | 7.10 | 8.39 | 8.82 |
| PPG-5 Laureth-5 | 13% | 6.96 | 7.79 | 8.07 |
| Steareth-2 (IPA) | 3% | 33.42 | 8.61 | 9.38 |
| Steareth-2 (IPA) | 6% | 7.13 | 8.37 | 9.21 |
| Steareth-2 (Hexanol) | 6% | 7.81 | 8.38 | 10.79 |

Example D

Distribution Test

Cover material similar to that used to produce a tampon was prepared by spraying a solution containing the designated amount (on a solids basis) of the chosen non-ionic treatment onto a 0.4 osy polypropylene spunbond web (see description in Example C). The sample was then dried in an oven before use and cut into eight inch lengths. An absorbent ribbon formed from a blend of ⅔ rayon and ⅓ cotton fibers was prepared and cut into eight inch lengths.

Eight inch lengths of the treated sample were weighed and each placed individually over an eight inch piece of the rayon/cotton absorbent. The treated cover was then insulted with 5 mL of a low viscosity menses solution at a rate of 10 mL/hr. The absorbent layer was then cut into eight one inch pieces and each sample was weighed to obtain a saturation profile of the particular treated sample. The fluid distribution was obtained by calculating the degree of saturation (amount liquid absorbed) for each one inch segment of a particular sample. For a given sample, a distribution profile can be constructed by adding the individual saturation segments together. The fluid distribution can be used to calculate a Saturation Ratio ("SR") for a given 8 inch absorbent strip. In the formula for "SR" shown below, each of the letters "A" through "H" represents the amount of liquid absorbed in a given one inch segment of the eight inch strip where the segments are labeled alphabetically (A–H) running consecutively from one end to the other of the strip.

$$SR=[(4*A)+(4*H)]/(D+E)+[(4*A)+(4*G)]/(D+E)+[(2*C)+(2*F)]/(D+E)$$

This method gives the highest weighting to a sample which evenly distributes a fluid over the entire eight inch length of the test strip. The ratio is calculated in the same manner as torque, where the fluid in each section is multiplied by the distance wicked by the fluid. This ratio gives higher values to materials which wick fluid the farthest. Due to the weighting used in the method, the SR evaluation scale will provide different values for samples of the same material of varying length. For samples of constant length, the specimen with the highest SR value distributes fluid the most effectively.

The Saturation Ratio as defined above, for each treated sample (at a variety of non-ionic add on levels) is shown in Table V below. There did not appear to be any significant differences for any of the non-ionic treatment examined as a function of concentration for each non-ionic treatment examined. A second method was used to corroborate the results obtained by the "SR" method. The average and standard deviation of the eight segments was calculated. The coefficient of variance ("COV"—standard deviation divided by the average) was then calculated for the eight segments. A COV value of "0" signifies that there were equal amounts of fluid in each of the eight segments, i.e., a perfectly flat distribution of fluid. Thus, for the "SR" method a higher value indicates better wicking performance, while the reverse is true for the COV-DSN test.

TABLE V

| Surfactant | Conc. (wt. %) | Sat. Ratio | COV-DSN |
|---|---|---|---|
| Laureth-4 | 3% | 1.51 | 4.11 |
| Laureth-4 | 6% | 1.51 | 4.11 |
| Laureth-4 | 9% | 1.51 | 4.11 |
| Laureth-4 | 13% | 1.51 | 4.11 |
| Glucopon 220 | 3% | 1.48 | 4.17 |
| Glucopon 220 | 6% | 1.48 | 4.17 |
| Glucopon 220 | 9% | 1.48 | 4.17 |
| Glucopon 220 | 13% | 1.48 | 4.17 |
| PPG-5 Laureth-5 | 3% | 1.62 | 4.12 |
| PPG-5 Laureth-5 | 6% | 1.62 | 4.12 |
| PPG-5 Laureth-5 | 9% | 1.62 | 4.12 |
| PPG-5 Laureth-5 | 13% | 1.62 | 4.12 |
| Steareth-2 (IPA) | 3% | 1.06 | 4.18 |
| Steareth-2 (IPA) | 9% | 1.62 | 4.18 |
| Steareth-2 (Hexanol) | 6% | 0.83 | 4.55 |

Example E

The effect of Glucopon 220 on growth of *S. aureus* and production of alpha-toxin (alpha-hemolysin) was determined by placing the desired concentration, expressed in millimoles/milliliter (millimolar hereinafter mM), in 100 mL of a growth medium in a sterile, 500 mL Corning fleaker™. Glucopon 220 was added directly to the growth medium, filter sterilized, and diluted in sterile growth medium to obtain the desired final concentrations.

The experiment was conducted following the procedure described in Example A except that the test organism in this example, *S. aureus* RN6390, was obtained from Dr. Richard Novick, The Skirball Institute for Biomolecular Medicine, New York University Medical Center, New York, N.Y. The experiment included fleakers of growth medium without Glucopon 220 (control) or with varying concentrations of Glucopon 220. Each fleaker was inoculated with *S. aureus* RN6390 following the procedure described in Example A. The fleakers were capped with sterile aluminum foil and incubated at 35° C. for 24 hours in atmospheric air in a Lab-Line orbital water bath at 180 rpm.

Five milliliters of the culture fluid was prepared for the analysis of alpha-hemolysin as follows: the culture fluid was adjusted to a standard absorbance (1.0) and centrifuged at 2500 rpm at 2–10° C. for 15 minutes. The supernatant was filter sterilized through an Autovial® 5 syringeless filter, 0.2 micron pore size (Whatman, Inc., Clifton, N.J.). The resulting fluid was frozen at −20° C. in a Fisherbrand®12×75 mm polystyrene culture tube, Fisher Scientific, 585 Alpha Drive, Pittsburgh, Pa. 15328.

The amount of alpha-hemolysin was determined by a hemolytic assay using rabbit red blood cells. The method employed was as follows: defibrinated rabbit red blood cells (rrbc; Remel) were washed 3 times in a Tris-saline buffer consisting of 50 mM Tris/Tris-HCl and 100 mM NaCl, pH 7.0. Centrifugation was at 800×g for 7 minutes. The reagents were obtained from Sigma Chemical Corporation. The rrbc were suspended in 200 mL Tris-saline buffer to a concentration of 0.5%. The culture supernatants were serially diluted in the culture medium. One part diluted sample was combined with 9 parts rrbc. All sample assays were run in triplicate. Controls for hemolysis consisted of a negative control (one part Tris-saline buffer to 9 parts rrbc) and a positive control (one part 10% SDS to 9 parts rrbc). Ten replicas of the controls were prepared. All assay samples were incubated at 37° C. for 30 minutes, then centrifuged at 800×g for 10 minutes. The amount of hemolysis in the samples and controls was measured at 405 nm in a BioTek Model EL309 microplate reader. Units of activity are expressed as the reciprocal of the dilution of each test sample giving 50% lysis.

The effect of Glucopon 220 on alpha-toxin production is shown in Table VI below.

TABLE VI

| Glucopon 220 (mM) | Alpha-hemolysin units | Alpha hemolysin (% of control) |
| --- | --- | --- |
| None | 32 | |
| 2 mM | 0 | 0.0% |
| 1 mM | 2.2 | 6.9% |
| 0.5 mM | 4.4 | 13.8% |

Example F

Tampon Fluid Distribution Test

Tampon prototypes containing a porous cover coated with either 7 wt. % Laureth-4, 18 wt. % PPG-5 Laureth-5, 8 wt. % Steareth-2 or 14 wt. % Glucopon 220 were produced according to the procedure described in Example B. The tampon prototypes were employed in actual use tests and analyzed to determine the percent surface stain on the outer surface (cover) and inner core (absorbent layer). A change-point regression model was used to predict the percent of internal and external stain area based on grams loading in the used product. In essence, the change-point model fits the data using two regression lines, one that describes the function between the percent area and grams loading up to the change-point and a second that describes the function beyond the change-point.

Figure 2:
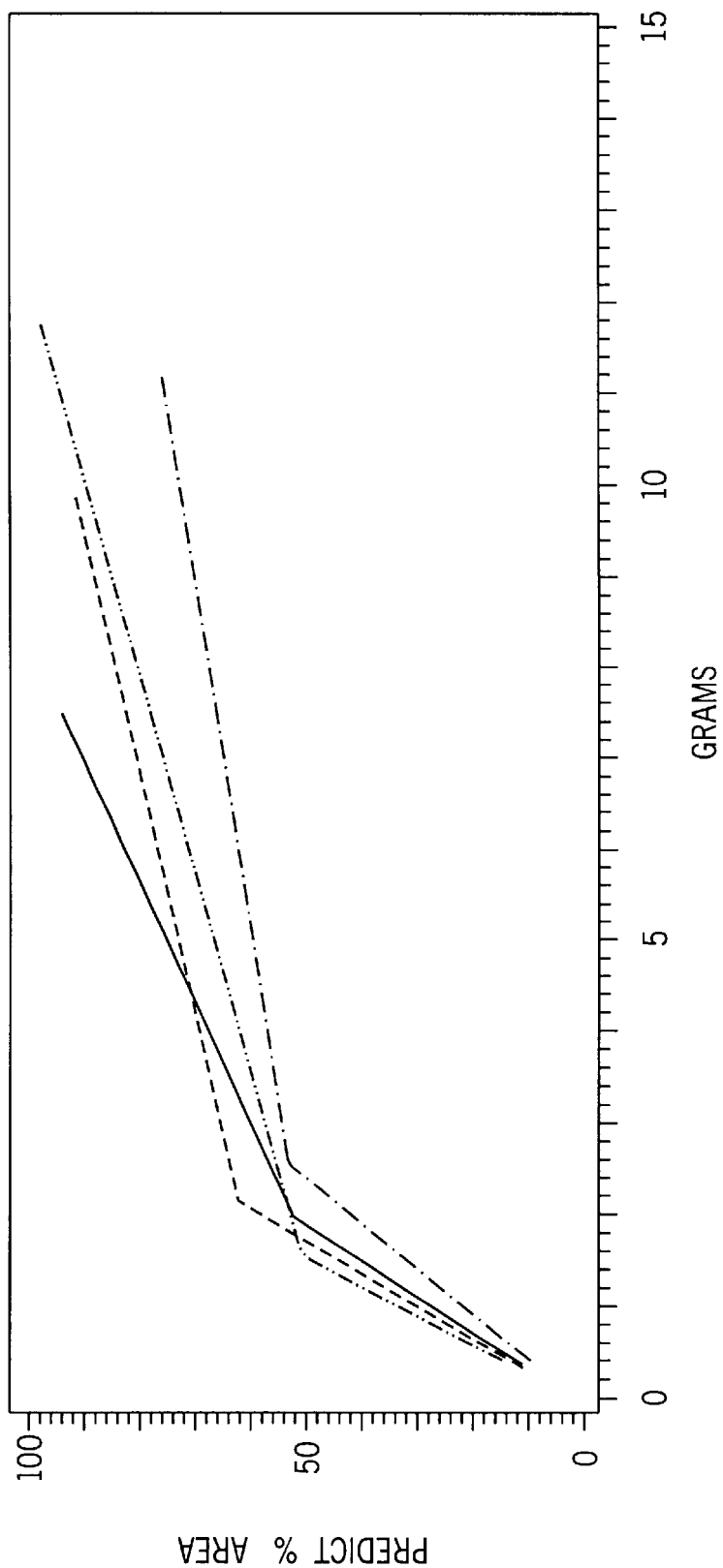
FIG. 2 is a graph showing the predicted percent stain area as a function of grams loaded for the external stain pattern for tampon prototypes with covers coated with various surface treatments. The codes for the graph correspond to the following treatments of the cover used to form the tampon protoptypes: L—7 wt. % Laureth-4; P—18 wt. % PPG-5 Laureth-5; S—8 wt. % Steareth-2; and T—14 wt. % Glucopon 220.

The results are shown in FIGS. 1 and 2 and in Tables VI and VII below. FIG. 1 is a graph showing the predicted percent stain area as a function of grams loaded for the internal stain pattern for prototypes with covers coated with various surface treatments. FIG. 2 is a graph showing the predicted percent stain area as a function of grams loaded for the external stain pattern for tampon prototypes with covers coated with various surface treatments. The results in Tables VII and VIII show that Glucopon 220 enhances the fluid distribution on both the outer surface and inner core. The results obtained with Glucopon 220 are substantially better than those for prototypes with covers treated with Steareth-2 and comparable to those observed for Laureth-4 and PPG-5 Laureth-5 treated tampon prototypes.

TABLE VII

| Surfactant (wt. %) | External Chge.-Pt. | External Slope Estimate | |
| --- | --- | --- | --- |
| | | 1st Line | 2nd Line |
| 7% Laureth-4 | 2.0 | 25.88 | 7.66 |
| 18% PPG-5 Laureth-5 | 2.2 | 28.28 | 3.78 |
| 14% Glucopon 220 | 1.6 | 31.77 | 4.58 |
| 8% Steareth-2 | 2.6 | 20.33 | 2.65 |

TABLE VIII

| Surfactant (wt. %) | Internal Chge.-Pt. | Internal Slope Estimate | |
| --- | --- | --- | --- |
| | | 1st Line | 2nd Line |
| 7% Laureth-4 | 3.6 | 17.69 | 7.25 |
| 18% PPG-5 Laureth-5 | 5.1 | 16.87 | 1.14 |
| 14% Glucopon 220 | 4.3 | 17.56 | 2.83 |
| 8% Steareth-2 | 4.9 | 16.10 | −0.96 |

Throughout this application various publications are referenced. The disclosures of these publications in their entireties are hereby incorporated by reference into this application in order to more fully describe the state of the art to which this invention pertains.

The invention has been described with reference to various specific and illustrative embodiments and techniques. However, it should be understood that many variations and modifications may be made while remaining within the spirit and scope of the invention.

What is claimed is:

1. A catamenial tampon comprising an absorbent material and an outer layer, the outer layer comprising from about 6 wt. % to about 10 wt. % of an alkyl polyglycoside, the alkyl polyglycoside being capable of inhibiting the production of exoprotein from Gram positive bacteria when said tampon is exposed to the bacteria.

2. A catamenial tampon comprising an absorbent tampon material and an outer tampon layer, the outer tampon layer comprising about 20 wt. % of an alkyl polyglycoside, the alkyl polyglycoside being capable of inhibiting the production of exoprotein from Gram positive bacteria when said tampon is exposed to the bacteria.

3. The tampon of claim 1 wherein the alkyl polyglycoside is capable of inhibiting the production of TSST-1 from *Staphylococcus aureus*.

4. The tampon of claim 1 wherein the alkyl polyglycoside is capable of inhibiting the production of alpha-toxin from *Staphylococcus aureus*.

5. The tampon of claim 1 wherein the outer layer is liquid permeable.

6. The tampon of claim 1 wherein the outer layer is an outer portion of the absorbent layer.

7. The tampon of claim 1 wherein the alkyl polyglycoside is distributed throughout the absorbent material.

8. The tampon of claim 1 wherein the alkyl polyglycoside has an alkyl group having from 8 to 18 carbon atoms.

9. The tampon of claim 8 wherein the alkyl group is a linear alkyl group.

10. The tampon of claim 8 wherein the alkyl polyglycoside has an alkyl group with 8 to 14 carbon atoms.

11. The tampon of claim 1 wherein the alkyl polyglycoside is an alkyl polyglucoside.

12. The tampon of claim 1 wherein the alkyl polyglycoside has an HLB of 10 to 15.

13. The tampon of claim 1 wherein the alkyl polyglycoside is represented by:

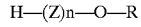

wherein "Z" is a saccharide residue having 5 or 6 carbon atoms, "n" is a number having a value in the range from 1 to 6, and R represents a linear alkyl group having 8 to 18 carbon atoms.

14. The tampon of claim 13 wherein R represents a linear alkyl group having 8 to 14 carbon atoms.

15. The tampon of claim 1 wherein the alkyl polyglycoside has an alkyl group with an average of 8 to 12 carbon atoms.

16. A catamenial tampon comprising absorbent material and a liquid-permeable cover wherein the liquid permeable cover comprises at least 6 wt. % alkyl polyglycoside based on a dry weight of the cover, the catamenial tampon being sized and configured for insertion into a vagina such that the outer layer is in contiguous relation with the inner wall of the vagina.

17. The tampon of claim 16 wherein the alkyl polyglycoside has an HLB of 12 to 15.

18. The tampon of claim 16 wherein the alkyl polyglycoside has a linear alkyl group having from 8 to 10 carbon atoms.

19. A catamenial tampon comprising absorbent material and a liquid-permeable cover wherein the liquid permeable cover comprises at least 6 wt. % alkyl polyglycoside based on a dry weight of the cover, and the alkyl polyglycoside has an HLB of 12 to 15 and an alkyl group with an average of 8 to 12 carbon atoms.

20. The tampon of claim 19 wherein the alkyl polyglycoside has a linear alkyl group having from 8 to 10 carbon atoms.

21. The tampon of claim 19 wherein the liquid-permeable cover is a porous nonwoven sheet.

22. The tampon of claim 21 wherein the porous nonwoven sheet is formed from fibers of hydrophobic polymer.

23. The tampon of claim 22 wherein the alkyl polyglycoside is coated on the fibers.

24. The tampon of claim 22 wherein the porous nonwoven sheet is a spunbond web formed from polypropylene or polyethylene fibers or a mixture thereof.

25. The catamenial tampon of claim 1 wherein the alkyl polyglycoside has an HLB of at least about 12.

26. The catamenial tampon of claim 1 wherein the alkyl polyglycoside has an HLB of from about 12 to about 14.

* * * * *

UNITED STATES PATENT AND TRADEMARK OFFICE
CERTIFICATE OF CORRECTION

PATENT NO. : 6,599,521 B1
DATED : July 29, 2003
INVENTOR(S) : Rasheski-Wedepohl et al.

It is certified that error appears in the above-identified patent and that said Letters Patent is hereby corrected as shown below:

Column 8,
Line 33, ""super-plus_size" should read -- "super-plus" size --.

Column 10,
Lines 62-63, "10 to 5 about 15." should read -- 10 to about 15.--.

Column 13,
Line 63, "S aureus" should read -- S. aureus --.

Column 14,
Line 28, "S aureus" should read -- S. aureus --.

Column 18,
Line 52, "was than subjected" should read -- was then subjected --.

Signed and Sealed this

Sixth Day of July, 2004

JON W. DUDAS
*Acting Director of the United States Patent and Trademark Office*